(12) United States Patent
Stone et al.

(10) Patent No.: US 9,910,041 B2
(45) Date of Patent: Mar. 6, 2018

(54) METHOD OF DETERMINING VIRUS REMOVAL FROM A SAMPLE CONTAINING A TARGET PROTEIN USING ACTIVATED CARBON

(71) Applicant: EMD Millipore Corporation, Burlington, MA (US)

(72) Inventors: Matthew T. Stone, Cambridge, MA (US); Ushma Mehta, Westford, MA (US); Damon Asher, Jefferson, MA (US); Patricia Greenhalgh, Bedford, MA (US)

(73) Assignee: EMD Millipore Corporation, Burlington, MA (US)

( * ) Notice: Subject to any disclaimer, the term of this patent is extended or adjusted under 35 U.S.C. 154(b) by 0 days.

(21) Appl. No.: 14/891,727

(22) PCT Filed: Apr. 4, 2014

(86) PCT No.: PCT/US2014/032940
§ 371 (c)(1),
(2) Date: Nov. 17, 2015

(87) PCT Pub. No.: WO2015/005961
PCT Pub. Date: Jan. 15, 2015

(65) Prior Publication Data
US 2016/0123981 A1    May 5, 2016

Related U.S. Application Data
(60) Provisional application No. 61/845,429, filed on Jul. 12, 2013.

(51) Int. Cl.
| | |
|---|---|
| *C07K 16/00* | (2006.01) |
| *C07K 1/36* | (2006.01) |
| *C07D 471/02* | (2006.01) |
| *C07K 1/16* | (2006.01) |
| *C07K 1/18* | (2006.01) |
| *G01N 33/569* | (2006.01) |
| *C07K 1/20* | (2006.01) |
| *C07K 1/22* | (2006.01) |
| *C12Q 1/04* | (2006.01) |
| *C12Q 1/06* | (2006.01) |

(52) U.S. Cl.
CPC ......... *G01N 33/56983* (2013.01); *C07K 1/20* (2013.01); *C07K 1/22* (2013.01); *C07K 16/00* (2013.01); *C12Q 1/04* (2013.01); *C12Q 1/06* (2013.01); *G01N 2333/015* (2013.01); *G01N 2333/15* (2013.01)

(58) Field of Classification Search
CPC .. A61K 31/56; A61K 2300/00; A61K 31/343; C07J 1/0011; C07J 1/0025
See application file for complete search history.

(56) References Cited

U.S. PATENT DOCUMENTS

| | | | |
|---|---|---|---|
| 31,093 A | 1/1861 | Smith | |
| 3,770,625 A | 11/1973 | Wallis et al. | |
| 4,116,768 A | 9/1978 | Isowa et al. | |
| 4,816,567 A | 3/1989 | Cabilly et al. | |
| 5,162,286 A | 11/1992 | MacDowall | |
| 5,204,310 A | 4/1993 | Tolles et al. | |
| 5,639,376 A | 6/1997 | Lee et al. | |
| 5,714,354 A | 2/1998 | Arnold et al. | |
| 6,783,713 B2 | 8/2004 | Tremblay et al. | |
| 7,390,403 B2 | 6/2008 | Siwak | |
| 8,123,940 B2 | 2/2012 | Sumian et al. | |
| 2006/0029612 A1 | 2/2006 | Palmer et al. | |
| 2006/0251761 A1 | 11/2006 | Jansen et al. | |
| 2006/0281075 A1 | 12/2006 | Smith et al. | |
| 2009/0186395 A1* | 7/2009 | Nur | A61L 2/0017 435/214 |
| 2010/0272755 A1 | 10/2010 | Costantino et al. | |
| 2011/0186505 A1 | 8/2011 | Diemer et al. | |
| 2012/0189605 A1 | 7/2012 | Koppaka et al. | |

FOREIGN PATENT DOCUMENTS

| | | |
|---|---|---|
| EP | 0087245 A2 | 8/1983 |
| EP | 0858831 A1 | 8/1998 |
| EP | 1251845 A1 | 10/2002 |
| EP | 1567188 A2 | 8/2005 |
| EP | 2184071 A1 | 5/2010 |
| JP | 49-76329 A | 7/1974 |
| JP | 05292986 A | 11/1993 |
| JP | 08225452 A | 9/1996 |
| JP | 09169648 A | 6/1997 |
| WO | 1992/010497 A1 | 6/1992 |
| WO | 1992/020702 A1 | 11/1992 |
| WO | 1996/002563 A1 | 2/1996 |
| WO | 1996/018745 A1 | 6/1996 |
| WO | 1996/040857 A1 | 12/1996 |

(Continued)

OTHER PUBLICATIONS

Matsushita et al., 2013, Separation and Purification technology, 107:79-84.*
Clark et al., "In Vitro Studies on the Use of Clay, Clay Minerals and Charcoal to Adsorb Bovine Rotavirus and Bovine Coronavirus", Veterinary Microbiology, Elsevier BV, NL, vol. 63, No. 2-4, Jan. 26, 1998, pp. 137-146.
Matsushita et al., "Adsorptive Virus Removal with Super-Powdered Activated Carbon", Separation and Purification Technology, Elsevier Science, vol. 107, 2013, pp. 79-84.
International Search Report Received for PCT Application No. PCT/US2014/032940, dated Sep. 2, 2014, 4 pages.
Fitzgeorge et al., "Immunospecific Isolation of Antibodies by Dissociation from Virus or Particulate Antigen Adsorbed on Charcoal", Immunochemistry, Pergamon Press, GB, vol. 10, Issue 1, Jan. 1973, pp. 21-29.
Bolton et al., "Normal-flow Virus Filtration: Detection and Assessment of the Endpoint in Bioprocessing", Biotechnology, Application Biochemistry, vol. 42, 2005, pp. 133-142.

(Continued)

*Primary Examiner* — Barry A Chestnut
(74) *Attorney, Agent, or Firm* — EMD Millipore Corporation (57) ABSTRACT

The present invention provides methods for determining whether activated carbon can be used for removing viruses or a certain virus from a sample containing a target protein.

16 Claims, 2 Drawing Sheets

(56) References Cited

FOREIGN PATENT DOCUMENTS

| WO | WO9640857 | * | 12/1996 |
|---|---|---|---|
| WO | 1997/003092 A1 | | 1/1997 |
| WO | 1997/021346 A1 | | 6/1997 |
| WO | 2008/118752 A2 | | 10/2008 |
| WO | 2012/051147 A1 | | 4/2012 |
| WO | WO2012051147 | * | 4/2012 |
| WO | 2013/028330 A2 | | 2/2013 |

OTHER PUBLICATIONS

Clackson et al., "Making Antibody Fragments Using Phage Display Libraries", Nature, vol. 352, Aug. 15, 1991, pp. 624-628.

Gueffroy, Donald E., "Buffers: A Guide for the Preparation and Use of Buffers in Biological Systems", Calbiochem-Behring Corporation, Copyright 1975, 24 pages.

Jones et al., "Replacing the Complementarity-Determining Regions in a Human Antibody with those from a Mouse", Nature, vol. 321, May 29, 1986, pp. 522-525.

Kohler et al., "Continuous Cultures of Fused Cells Secreting Antibody of Predefined Specificity", Nature, vol. 256, Aug. 7, 1975, pp. 495-497.

Marks et al., "By-passing Immunization Human Antibodies from V-gene Libraries Displayed on Phage", Journal of Molecular Biology, vol. 222, 1991, pp. 581-597.

Morrison et al., "Chimeric Human Antibody molecules: Mouse Antigen-Binding Domains with Human Constant Region Domains", Proc. Natl.. Acad. Sci. USA, vol. 81, Nov. 1984, pp. 6851-6855.

Presta, Leonard G., "Antibody Engineering", Current Opinion in Structural Biology, vol. 2, No. 4, 1992, pp. 593-596.

Riechmann et al., "Reshaping Human Antibodies for Therapy", Nature, vol. 332, Mar. 24, 1988, pp. 323-327.

Spearman, C., "The Method of 'Right and Wrong Cases' ('Constant Stimuli') without Gauss's Formulae", British Journal of Psychology, vol. 2, 1908, pp. 227-242.

"Harmonized Tripartate Guideline: Q5A Viral Safety of Biotechnology Products Derived From Cell Lines of Human or Animal Origin", Published in the Federal Register, vol. 63, No. 185, Sep. 23, 1999, 31 pages.

Brough et al.,"Performance of a Novel Viresolve NFR Virus Filter", Biotechnology Prog., 2002, vol. 18, No. 4, pp. 782-795.

Liu et al.,"Development and Qualification of a Novel Virus Removal Filter for Cell Culture Applications", Biotechnology Prog., 2000, vol. 16, No. 3, pp. 425-434.

* cited by examiner

METHOD OF DETERMINING VIRUS REMOVAL FROM A SAMPLE CONTAINING A TARGET PROTEIN USING ACTIVATED CARBON

FIELD OF THE INVENTION

The present invention relates to methods of determining whether activated carbon can be used for the removal of viruses from a sample containing a target protein.

BACKGROUND

The most commonly used processes for purifying target proteins such as, e.g., monoclonal antibodies, typically employ an engineered cell line (e.g., a mammalian or a non-mammalian cell line) capable of expressing the target protein. Such a target protein may either be secreted into the cell culture media or it may be expressed intracellularly and recovered following lysis of cells expressing the protein.

The target protein typically needs to be subjected to a series of purification steps to separate the target protein from various impurities, e.g., cells, cell debris, DNA, host cell proteins etc.

A typical purification process usually entails subjecting the cell culture feed or media (in case of a secretory target protein) or cell lysate (in case of an intracellular target protein) to a variety of steps, including one or more chromatography steps to isolate or purify the target protein. For example, in case of a secretory target protein, e.g., a monoclonal antibody, the cell culture media is typically subjected to a clarification step followed by a capture step followed by one or more of a cation exchange bind/elute chromatography step and an anion exchange chromatography step.

CHO cells are commonly used for the production of monoclonal antibodies. A typical CHO cell culture feed contains $10^3$ to $10^9$ viruses or virus-like particles and the removal of such viruses or virus-like particles is especially important during the purification process, as many of the target proteins are therapeutic proteins which are directly administered to patients. Generally, virus removal is evaluated based on the amount of total virus removal achieved by the entire purification process, which is desirable to be equal to or exceeding 18 logs, especially in cases where regulatory approval is required.

Generally, each step of a typical purification process is shown to remove some amount of viruses, however, the amount is usually less than 18 logs; and therefore, additional purification steps must be included in the process for adequate virus removal. It is important to establish whether or not a particular purification step can remove a certain amount of virus in order to ensure that adequate virus removal is achieved by the various purification steps in a purification process.

Guidance for virus safety evaluation of samples, e.g., biotechnology products, can be found in "Harmonized Tripartate Guideline: Q5A Viral Safety of Biotechnology Products Derived From Cell Lines of Human or Animal Origin. Fed. Reg. 63(185) 24 Sep. 1998," prepared under the auspices of the International Conference on Harmonization of Technical Requirements for Registration of Pharmaceuticals for Human Use (ICH).

Activated carbon has previously been used in water purification applications to remove viruses as well has been incorporated in filtration units for non-specific removal of substances, which may include viruses, from biological fluids, e.g., blood (e.g., see, U.S. Pat. No. 8,123,940).

Further, U.S. patent application Ser. No. 13/565,463, filing date Aug. 2, 2012, incorporated by reference herein in its entirety, describes the use of activated carbon in combination with other media for removal of proteinaceous impurities (e.g., host cell proteins) and DNA from a sample containing a biomolecule of interest (e.g., an antibody).

Lastly, U.S. Provisional Patent Application Ser. No. 61/769,269, filing date Feb. 26, 2013, incorporated by reference herein, describes the use of activated carbon for the selective removal of a protein from a mixture of proteins by changing solution conditions.

SUMMARY OF THE INVENTION

The present invention is based, at least in part, on the surprising and unexpected discovery that activated carbon can be used for reducing the amount of viruses in case of certain samples containing a target protein, e.g., a monoclonal antibody. Although, activated carbon has previously been described as removing some viruses during water purification, the samples that are treated with activated carbon generally have a low concentration of protein or no protein at all. The present invention is based, at least in part, on the unexpected and surprising discovery that activated carbon specifically binds viruses, including parvoviruses, retroviruses and retrovirus-like particles, in certain samples that include a high protein concentration (e.g., cell culture feed or cell lysate containing a target protein to be isolated). Therefore, the inclusion of activated carbon in certain purification processes can result in the potential elimination of one or more expensive chromatography steps (e.g., a cation exchange bind/elute chromatography step) that are typically used during protein purification.

In various embodiments, a method for determining whether activated carbon can be used for the removal of viruses from a sample containing a target protein is provided, where the method comprising the steps of: (a) providing a portion of the sample comprising a target protein; (b) adding a virus to the portion of the sample in the amount ranging from $10^4$ to $10^9$ PFU/mL; (b) flowing the portion of the sample through a column packed with activated carbon; (c) collecting one or more fractions containing the target protein from the column; and (d) measuring the virus amount in the one or more fractions, wherein a reduction in the virus amount in one or more fractions by at least 3.0 LRV is indicative that activated carbon can be used for removing viruses from the sample.

In some embodiments the sample comprises a protein concentration equal to or greater than 0.2 g/L. In some embodiments, the sample comprises a pH in the range of 3.0-10.0 and/or a salt concentration less than 0.5M.

In some embodiments, the sample comprises a cell culture feed. In a particular embodiment, the cell culture feed is a CHO cell culture feed.

In some embodiments, the sample comprises a cell culture feed that has been subjected to clarification. Clarification methods include, but are not limited to, centrifugation, settling, depth filtration, screen filtration, flocculation, use of a stimulus responsive polymer and pH change.

In some embodiments, the sample comprises an eluate recovered from a Protein A chromatography step used during the purification of the target protein.

In some embodiments, the sample comprises a cell lysate obtained from cells expressing a target protein intracellularly.

In some embodiments, the target protein is a recombinant protein. Exemplary target proteins include, but are not limited to, immunoglobulins, e.g., a monoclonal antibody, Fc-containing proteins as well as non-immunoglobulin proteins.

In a particular embodiment, the target protein is a therapeutic protein.

DETAILED DESCRIPTION

As discussed above, the present invention is based, at least in part, on the novel and unexpected discovery that activated carbon can be used for the removal of viruses from certain high protein concentration samples such as, e.g., certain cell culture feeds or cell lysates comprising a target protein to be purified.

The typical concentrations of virus in a bioreactor feed containing a therapeutic protein are generally very low. However, these low levels may still be dangerous to a patient being treated with the purified therapeutic protein. In order to ensure adequate removal of viruses during protein purification, it is important to determine whether a certain purification step will remove viruses from a sample containing a protein to be purified and also determine the amount of the virus removed by such purification step.

In order to do so, a representative virus is spiked into a solution containing a therapeutic protein at a known concentration and then the virus spiked solution of therapeutic protein is be subjected to a certain purification step. Following the purification step, the amount of the representative virus in the solution is determined. Adequate virus removal by the purification step is indicated by the level of virus being lower than detection limits for that virus or being undetectable in the solution following the purification step. Parvoviruses and retroviruses are two types of viruses that are generally measured during the purification of therapeutic proteins expressed in CHO cells.

Typically, a method used to determine the amount of virus removed from a sample containing a protein during a purification step employs a portion of the sample instead of the entire sample volume. Once a determination is made that a particular purification step is able to remove viruses from a portion of a sample containing a target protein, it can be assumed that the purification step will remove viruses from the sample, as long as the ratio of the purification media employed and the target protein are kept the same.

The present invention provides methods for determining whether activated carbon can be used for the removal of certain viruses from certain samples. As demonstrated in the Examples herein, using the methods described herein, it can be determined whether activated carbon is able to remove viruses from a particular sample containing a target protein. Therefore, for those samples containing a target protein, where activated carbon is able to remove viruses, activated carbon can subsequently be incorporated in the purification process for that sample.

In order that the present disclosure may be more readily understood, certain terms are first defined. Additional definitions are set forth throughout the detailed description.

I. Definitions

The term "active carbon" or "activated carbon," as used interchangeably herein, refers to a carbonaceous material which has been subjected to a process to enhance its pore structure. Activated carbon is sometimes also referred to as activated charcoal. Activated carbons are porous solids with very high surface areas. They can be derived from a variety of sources including coal, wood, coconut husk, nutshells, and peat. Activated carbon can be produced from these materials using physical activation involving heating under a controlled atmosphere or chemical activation using strong acids, bases, or oxidants. The activation processes produce a porous structure with high surface areas that give activated carbon high capacities for impurity removal. Activation processes can be modified to control the acidity of the surface.

Typical activation processes involve subjecting a carbon source, such as, resin wastes, coal, coal coke, petroleum coke, lignites, polymeric materials, and lignocellulosic materials including pulp and paper, residues from pulp production, wood (like wood chips, sawdust, and wood flour), nut shell (like almond shell and coconut shell), kernel, and fruit pits (like olive and cherry stones) to a thermal process (e.g., with an oxidizing gas) or a chemical process (e.g., with phosphoric acid or metal salts, such as zinc chloride). An exemplary process involving chemical activation of wood-based carbon with phosphoric acid ($H_3PO_4$) is disclosed in U.S. Pat. No. Re. 31,093, which resulted in an improvement in the carbon's decolorizing and gas adsorbing abilities. Also, U.S. Pat. No. 5,162,286 teaches phosphoric acid activation of wood-based material which is particularly dense and which contains a relatively high (30%) lignin content, such as nut shell, fruit stone, and kernel. Phosphoric acid activation of lignocellulose material is also discussed in U.S. Pat. No. 5,204,310, as a step in preparing carbons of high activity and high density. The teachings of each of the patents listed in this paragraph are incorporated by reference herein in their entirety.

In contrast to most other adsorbing materials, activated carbon is believed to interact with molecules using relatively weak Van der Waals or London dispersion forces. Typical commercial activated carbon products exhibit a surface area of at least 300 $m^2/g$, as measured by the nitrogen adsorption based Brunauer-Emmett-Teller ("BET") method, which is method well known in the art.

Although, active or activated carbon has been previously employed in processes for purifying liquids and gases as well as for purifying a recombinantly expressed antibody from other impurities by binding to impurities, it has not been previously employed for removing viruses, especially parvoviruses and retroviruses, from high protein concentration samples (i.e., >0.2 g/L, protein concentration). Consequently, activated carbon provides a cost effective solution, in some instances, for the removal of viruses during processes for purifying therapeutic proteins, e.g., monoclonal antibodies.

The present invention provides methods to determine whether or not activated carbon can be used for removal of viruses from a sample containing a target protein. Because activated carbon does not result in effective removal of viruses in case of all samples, based on the methods provided herein, it can be readily determined as to in case of which samples, activated carbon can be used for removal of viruses or a particular type of virus.

The terms "protein of interest" and "target protein," as used interchangeably herein, refer to a protein or polypeptide, which is to be purified from a composition containing viruses. In some embodiments, the target protein is a therapeutic protein to be administered to a patient.

In general, the overall purity of the target protein increases as a result of virus removal. The target protein may be an immunoglobulin or a non-immunoglobulin protein and may be a secretory protein or an intracellular protein. In some embodiments, the target protein is an immunoglobulin protein, e.g., a monoclonal antibody.

Other examples of target proteins include recombinant proteins which include, but are not limited to, recombinant human growth hormone, recombinant human insulin, recombinant follicle-stimulating hormone, recombinant factor VII (anti-hemophilic factor), recombinant human erythropoietin, recombinant granulocyte colony-stimulating factor, recombinant alpha-galactosidase a, recombinant iduronidase, recombinant galsulfase, recombinant dornase alfa, recombinant tissue plasminogen activator, recombinant human interferons, recombinant insulin-like growth factor 1, and recombinant asparaginase.

In other embodiments of this invention, target proteins are proteins derived from human blood or other physiological fluids. Examples of such proteins include, but not limited to, immunoglobulins G and M, Factor VIII, Factor IX, anti-thrombin III, and alpha-I-antitrypsin.

The term "immunoglobulin," "Ig" or "IgG" or "antibody" (used interchangeably herein) refers to a protein having a basic four-polypeptide chain structure consisting of two heavy and two light chains, said chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen.

The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of antibody light chains are referred to interchangeably as "light chain constant regions", "light chain constant domains", "CL" regions or "CL" domains. The "constant" domains of antibody heavy chains are referred to interchangeably as "heavy chain constant regions", "heavy chain constant domains", "CH" regions or "CH" domains. The "variable" domains of antibody light chains are referred to interchangeably as "light chain variable regions". "light chain variable domains", "VL" regions or "VL" domains. The "variable" domains of antibody heavy chains are referred to interchangeably as "heavy chain variable regions", "heavy chain variable domains", "VH" regions or "VH" domains.

Immunoglobulins or antibodies may be monoclonal or polyclonal and may exist in monomeric or polymeric form, for example. IgM antibodies which exist in pentameric form and/or IgA antibodies which exist in monomeric, dimeric or multimeric form. Immunoglobulins or antibodies may also include multispecific antibodies (e.g., bispecific antibodies).

The term "Fc region" and "Fc region containing protein" means that the protein contains heavy and/or light chain constant regions or domains (CH and CL regions as defined previously) of an immunoglobulin. Proteins containing an "Fc region" can possess the effector functions of an immunoglobulin constant domain. An "Fc region" such as $CH_2/CH_3$ regions, can bind selectively to affinity ligands such as Protein A or functional variants thereof. In some embodiments, an Fc region containing protein specifically binds Protein A or a functional derivative, variant or fragment thereof. In other embodiments, an Fc region containing protein specifically binds Protein G or Protein L, or functional derivatives, variants or fragments thereof.

As discussed above, in some embodiments, a target protein is an Fc region containing protein. e.g., an immunoglobulin. In some embodiments, an Fc region containing protein is a recombinant protein which includes the Fc region of an immunoglobulin fused to another polypeptide or a fragment thereof.

Generally, an immunoglobulin or antibody is directed against an "antigen" of interest. Preferably, the antigen is a biologically important polypeptide and administration of the antibody to a mammal suffering from a disease or disorder can result in a therapeutic benefit in that mammal.

The term "monoclonal antibody" or "Mab," as used interchangeably herein, refers to an antibody obtained from a population of substantially homogeneous antibodies, i.e., the individual antibodies in the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). "Monoclonal antibodies" may also be isolated from phage antibody libraries using the techniques described in Clackson et al., Nature 352:624-628 (1991) and Marks et al., J. Mol. Biol. 222:581-597 (1991). Monoclonal antibodies may also be referred to as "MAbs" or "mabs" or "mAbs" or "MABs."

Monoclonal antibodies may further include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances. Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody may comprise at least a portion of an immunoglobulin constant region (Fc), typically that of a human immunoglobulin. For further details, see Jones et al., Nature 321:522-525 (1986); Riechmann et al., Nature 332: 323-329 (1988); and Presta, Curr. Op. Struct. Biol. 2:593-596 (1992).

The term "solution" or "sample," as used herein, refers to a composition containing a target protein which is subjected to virus removal using activated carbon, once it is demonstrated using the methods described herein that activated carbon can be used for removing viruses from the composition. In some embodiments, the sample comprises cell culture feed, for example, feed from a mammalian cell culture (e.g., CHO cells) expressing a secretory target protein. e.g., a monoclonal antibody. In some embodiments, the sample comprises a cell lysate obtained from mammalian or non-mammalian cells expressing a target protein intracellularly. In some embodiments, the sample comprises a cell culture feed that has been subjected to clarification. In some embodiments, the sample comprises an eluate from a Protein A affinity chromatography column. Samples also encompass non-mammalian expression systems used for producing a protein of interest or target protein.

The term "non-mammalian expression systems," as used herein, refers to all host cells or organisms employed to generate therapeutic proteins, where the host cells or organisms are of non-mammalian origin. Examples of non-mammalian expression systems used for producing a protein of interest or target protein include yeast such as, *Saccharomyces cerevisiae* and *Pichia pastoris*, bacteria such as *Escherichia coli, Bacillus megaterium, Brevibacillus choshinensis*, insect cells such as *Spodoptera frugiperda* cells, Baculovirus infected insect cells, and algae cells.

The term "portion of a sample" refers to part of a sample containing a target protein which is used to determine whether activated carbon can be used to remove viruses from the sample, as described herein. In general, once it is demonstrated that activated carbon is able to remove viruses or a certain type of virus from a part of a sample containing a target protein, activated carbon can then be incorporated into a purification process for the target protein in order to remove viruses or a certain type of virus from the sample.

The terms "clarify." "clarification," and "clarification step," as used herein, refers to a process step for removing suspended particles and or colloids, thereby to reduce turbidity, of a target protein containing solution, as measured in NTU (nephelometric turbidity units). Clarification can be achieved by a variety of means, including centrifugation or filtration. Centrifugation could be done in a batch or continuous mode, while filtration could be done in a normal flow (e.g. depth filtration) or tangential flow mode. In processes used in the industry today, centrifugation is typically followed by depth filtration intended to remove insoluble impurities, which may not have been removed by centrifugation. Furthermore, methods for enhancing clarification efficiency can be used, e.g. precipitation. Precipitation of impurities can be performed by various means such as by flocculation, pH adjustment (acid precipitation), temperature shifts, phase change due to stimulus-responsive polymers or small molecules, or any combinations of these methods. In some embodiments described herein, clarification involves any combinations of two or more of centrifugation, filtration, depth filtration and precipitation.

The terms "purifying," "increasing the purity," "separating," or "isolating," as used interchangeably herein, refer to increasing the ratio of target protein to one or more viruses in a sample by removing the one or more viruses from the sample. Typically, once it is determined that activated carbon can be used for removing viruses from a sample containing a target protein, as described herein, activated carbon is included in the process for purifying that target protein, thereby to increase the purity of the target protein.

The term "virus" or "viruses" refers to small infectious agents or particles that can replicate only inside a living cell. They are generally composed of nucleic acid (RNA or DNA) enclosed inside a protein capsid, and optionally, a lipid envelope.

The term "parvovirus" refers to linear, non-segmented single-stranded DNA nonenveloped viruses, with an average genome size of 5000 nucleotides and a diameter of 18-26 nm. An exemplary parvovirus used in the methods described herein is minute virus of mice.

The term "retrovirus" refers to an RNA virus which is capable of integrating its genetic information into the genomic DNA of infected cells via a reverse-transcribed DNA intermediate. The term "retrovirus-like particle" refers to particles generated by cells that have portions of retrovirus-derived DNA in their genome. These particles resemble retroviruses, but are often noninfectious. The xenotropic murine leukemia virus, used in the Examples herein, represents a model retrovirus or retrovirus-like particle.

As used herein, the term "remove," "removing," "removal," "reduce." "reducing" or "reduction," as used interchangeably herein, refer to lowering the amount of one or more viruses in a sample which contains a target protein to be purified. As demonstrated herein, activated carbon can be used to remove one or more viruses from certain samples containing a target protein to be purified.

The terms "flow-through process," "flow-through mode," and "flow-through chromatography," as used interchangeably herein, refer to a product separation technique in which at least one product in a sample is intended to flow through activated carbon (e.g., target protein), while at least one potential component binds to the activated carbon (e.g., viruses).

The sample intended to flow through is generally referred to as the "mobile phase." The "flow-through mode" is generally an isocratic operation (i.e., a process during which the composition of the mobile phase is not changed). The media used for flow-through is usually pre-equilibrated with the same buffer solution that contains the target protein molecule. After purification, the media can be flushed with additional quantity of the same buffer to increase the product recovery.

The term "buffer" refers to a solution that resists changes in pH by the action of its acid-base conjugate components. Various buffers which can be employed in the methods described herein are described in Buffers. A Guide for the Preparation and Use of Buffers in Biological Systems, Gueffroy, D., ed. Calbiochem Corporation (1975). Different buffers maintain different ranges of pH, for example phosphate buffer is usually used for pH between 6.0 and 8.0, while for a higher pH, a borate buffer can be used, and for lower pH, a carbonate buffer can be used. Persons of ordinary skill in the art will be able to readily identify a suitable buffer to use, depending on the pH to be maintained. Non-limiting examples of buffers that can be used in the methods according to the present invention include MES, MOPS, MOPSO, Tris, HEPES, phosphate, acetate, citrate, succinate, carbonate, borate, and ammonium buffers, as well as combinations of these.

The term "wash buffer" or "equilibration buffer" are used interchangeably herein, refers to a buffer used to wash or re-equilibrate the activated carbon material prior to contacting a sample with the activated carbon.

The term "conductivity" refers to the ability of an aqueous solution to conduct an electric current between two electrodes. In solution, the current flows by ion transport. Therefore, with an increasing amount of ions present in the aqueous solution, the solution will have a higher conductivity. The unit of measurement for conductivity is milliSiemens per centimeter (mS/cm or mS), and can be measured using a commercially available conductivity meter (e.g., sold by Orion). The conductivity of a solution may be altered by changing the concentration of ions therein. For example, the concentration of a buffering agent and/or concentration of a salt (e.g. NaCl or KCl) in the solution may be altered in order to achieve the desired conductivity. Preferably, the salt concentration of the various buffers is modified to achieve the desired conductivity as in the Examples below.

The term "fraction" or "fractions" refers to a small volume of liquid collected after subjecting a sample containing a target protein to a purification step, e.g., flowing the sample through an activated carbon column. In the methods described herein, fractions are collected from an activated carbon column following the loading of the column with a portion of a sample containing a target protein. A fraction is used to monitor the amount of impurities, such as viruses, that are passing through the column at a particular point. It is typically expected that the amount of impurities that pass through a column will increase as the amount of the protein passed through the column is increased. The amount of protein in a sample which may be processed by a known amount of material used in a purification step, e.g., activated carbon, can be determined by collecting one or more fractions and determining the level of impurities, e.g., viruses, removed by that known amount of material.

The term "column load" or "load." as used herein, is the value corresponding to the mass of the target protein in solution that has passed through a column divided by the volume of the column. The mass of the target protein that has passed through the column is calculated by multiplying the concentration of the target protein in a sample by the volume of sample collected from the column.

The term "log removal value" or "LRV" is a value that represents the levels of impurities removed by a column when a known amount of impurity is passed through. $LRV=\log(C_f)-\log(C_p)$, where $C_f$ is the concentration of impurities in the feed solution and $C_p$ is the concentration of impurities in the feed solution after it has that has passed through the column.

II. Exemplary Activated Carbon Materials for Use in the Methods Described Herein Based on the methods described herein which employ activated carbon, it can be determined whether or not activated carbon can be used for the removal of viruses, including parvoviruses and retroviruses, from a sample containing a target protein. In some embodiments, activated carbon comprises activated charcoal. Activated carbon can be derived from a variety of sources including, but not limited to, coal, wood, coconut husk, nutshells, and peat. Activated carbon can be produced from these materials by physical activation involving heat under a controlled atmosphere or by chemical activation using strong acids, bases, or oxidants. The activation processes produce a porous structure with a high surface area that gives activated carbon a greater capacity for impurity removal. Activation processes can be modified to control the acidity of the surface.

Activated carbon is available from a wide variety of commercial sources and comes in a number of grades and formats. Some of the commercial suppliers of activated carbon include companies such as MeadWestVaco Corp., Richmond, Va., USA; Norit Americas Inc., Marshall, Tex., USA; Calgon Carbon Corp., Pittsburgh, Pa., USA.

In some embodiments described herein, activated carbon is incorporated in a cellulose-containing fibrous media.

Commercially available activated carbon materials that may be employed in the methods according to the present invention include, but are not limited to, Nuchar HD activated carbon (MeadWestVaco Corporation. Richmond, Va., USA); Nuchar SA 20 (MeadWestVaco Corporation, Richmond, Va., USA); Nuchar SN (MeadWestVaco Corporation, Richmond, Va., USA); Nuchar WV-B 30 (MeadWestVaco Corporation, Richmond, Va., USA); RGC Powder activated carbon (MeadWestVaco Corporation, Richmond, Va., USA); Norit Darco KB-G activated carbon (Norit Americas Inc., Marshall, Tex., USA); Norit CGP Super activated carbon (Norit Americas Inc., Marshall, Tex., USA); Norit A Supra USP (Norit Americas Inc., Marshall, Tex., USA); Norit E Supra USP (Norit Americas Inc., Marshall, Tex., USA); Norit C GRAN (Norit Americas Inc., Marshall, Tex., USA);

Norit SX Ultra (Norit Americas Inc., Marshall, Tex., USA); and Chemviron Pulsorb PGC activated carbon (Chemviron Carbon, Feluy, Belgium).

Two major formats of activated carbon are powdered and granular. Powdered activated carbon contains small and usually less than 1 mm diameter particles, and is most commonly used for purification of liquids. Granular activated carbon has a larger particle size and consequently a smaller surface area, so it is preferred for use in gas purification where the rate of diffusion is faster.

An important consideration for safety with use of activated carbon in consumer applications (such as water, food, beverage, and pharmaceutical purification) is reduction and control of extractable compounds. Activated carbon intended for drinking water and food contact applications is usually made in compliance with safety standard ANSI/NSF Standard 61 that covers all indirect additives to water. Also, ASTM standard test method D6385 describes determining acid extractable content in activated carbon by ashing and could be used to study and minimize the level of extractables from activated carbon.

A range of activated carbon types is available for various applications. For example, MeadWestVaco Corp. supplies at least twelve types of powdered activated carbon that vary by their capacity, surface acidity, pore accessibility to target molecules, and intended application. It is generally desirable to maximize the capacity of activated carbon for impurity removal.

III. Exemplary Viruses Used in the Methods Described Herein

Exemplary viruses that may be used in the methods described herein, include but are not limited to, Adenovirus, Calicivirus, Transmissible Gastroenteritis Virus, Bovine Diarrhea Virus, West Nile Virus, Duck Hepatitis B Virus, Cytomegalovirus, Herpes Simplex Virus, Infectious Bovine Rhinotracheitis Virus, Pseudorabies Virus, Influenza Virus, Simian Virus Type 40, Parainfluenza Virus, Human Parvovirus, Minute Virus of Mice, Porcine Parvovirus, Canine Parvovirus, Encephalomyocarditis Virus, Hepatitis A Virus, Poliovirus, Bovine Enterovirus, Porcine Enterovirus, Vaccinia Virus, Reovirus, Murine Leukemia Virus (Xenotropic, Amphotropic, Ecotropic). Human Immunodeficiency Virus, Vesicular Stomatitis Virus, Sindbis Virus and Semliki Forest Virus.

A virus is added to a portion of a sample containing a target protein in the amount ranging from $10^4$ to $10^8$ PFU/mL or TCID50/mL prior to the portion of sample being contacted with activated carbon, as described herein.

In some embodiments, the minute virus of mice, which represents a parvovirus, is added to a portion of sample containing a target protein. In other embodiments, the xenotropic murine leukemia virus, which represents a retrovirus or a retrovirus-like particle, is added to a portion of sample containing a target protein.

IV. Flow-Through Processes Using Activated Carbon

One general flow-through procedure which may be used for determining the removal of viruses using activated carbon is described below.

In some embodiments, a chromatography device, e.g., a column, is loaded with an aqueous slurry of activated carbon. Activated carbon can also be loaded into a device, e.g., a column, as a dry powder and then wetted with an aqueous solution. However, sometimes it may be challenging to remove small air bubbles from in between the activated carbon particles when the column is dry packed. The column is then equilibrated with a buffer having the same pH as the sample containing the target protein. The sample is subsequently passed through the activated carbon column at a flow-rate that results in a column residence time of between 15 secs and 10.0 mins. The eluate containing the target protein is subsequently collected.

V. Methods of Measuring the Amount of Viruses in Samples

Once a portion of sample is treated with activated carbon, as described herein, the amount of virus remaining in the sample is measured using one or more methods described herein or those known in the art. These methods include, but are not limited to, 50% tissue culture infectious dose (TCID50) assay, plaque-forming unit assay, focus-forming unit assay, 50% lethal dose assay, hemagglutination assay, florescent focus assay (FFA), bicinchoninic acid assay (BCA), single radial immunodiffusion assay (SRID), quantitative polymerase chain reaction (qPCR), enzyme-linked immunosorbent assay (ELISA), transmission electron microscopy. Generally, the method that is used would be dependent on the virus that is being measured or detected. Some of the assays which may be incorporated in the methods described herein are described below.

50% tissue culture infective dose (TCID50) is an endpoint dilution assay which quantifies the amount of virus required to kill 50% of infected host cells or to produce a cytopathic effect in 50% of inoculated tissue culture cells. Following incubation, the percentage of cell death (i.e. infected cells) is manually observed and recorded for each virus dilution and the results are used to mathematically calculate the TCID50.

Viral plaque-forming unit assays determine the number of plaque forming units (PFUs) in a sample by spreading various dilutions of the sample across confluent monolayers of host cells, and then, after a suitable incubation period (generally 3-14 days), counting the number of plaques in the monolayer.

A 50% lethal dose (LD50) assay is conducted by administering dilutions of a sample into suitable host animals to determine the dose that is sufficient to kill 50% of the animals.

The hemagglutination assay may be used to quantify certain viruses (e.g. influenza) by incubating serial dilutions of the sample with a 1% erythrocyte solution for one hour and then visually determining the virus dilution at which agglutination first occurs.

Fluorescent focus assays are conducted similarly to plaque-forming unit assays, except that the number of infectious units is determined by staining the cell monolayer with fluorescent antibodies that specifically bind to virus components. Fluorescence microscopy is used to count and quantify how many cells are infected.

A bicinchoninic acid assay (BCA) quantifies virus by measurement of the total amount of protein in a sample. BCA reagent is added to the sample, and a protein's peptide bonds quantitatively reduce $Cu^{2+}$ to $Cu^{1+}$, which produces a light blue color. BCA chelates $Cu^{1+}$ at a 2:1 ratio resulting in a more intensely colored species that absorbs at 562 nm. Absorbance of a sample at 562 nm is used to determine the bulk protein concentration in the sample. Assay results are compared with known standard curves after analysis with a spectrophotometer or plate reader.

Single radial immunodiffusion assay (SRID), also known as the Mancini method, is a protein assay that detects the amount of specific viral antigen by immunodiffusion in a semi-solid medium (e.g. agar). The medium contains an antiserum specific to the antigen of interest and the antigen is placed in the center of the disc. As the antigen diffuses into the medium it creates a precipitate ring that grows until a equilibrium is reached. Assay time can range from 10 hours to several days depending on the equilibration time of the antigen and antibody. The zone diameter from the ring is linearly related to the log of protein concentration and is compared to zone diameters for known protein standards for quantification.

Quantitative polymerase chain reaction (qPCR) is a technique that measures the amount of specific nucleic acid sequences in a sample. By using probes specific for viral genetic sequences, the number of viral genomes in a sample may be counted.

Transmission electron microscopy (TEM) may also be used to quantify virus by generation of high resolution magnified images of the sample. TEM images can show individual virus particles and quantitative image analysis can be used to determine virus concentration.

This invention is further illustrated by the following examples which should not be construed as limiting. The contents of all references, patents and published patent applications cited throughout this application, as well as the Figures, are incorporated herein by reference.

EXAMPLES

Example 1. The Production of Minute Virus of Mice

This example describes the process to prepare minute virus of mice (MVM), which represents a parvovirus. The MVM is subsequently spiked into solutions of MAB and its selective removal by activated carbon is examined.

High titer MVM is generated by infecting confluent A9 cells (ATCC CCL-1.4) in Advanced/F12 Dulbecco's Modified Eagle's Medium (DMEM) Invitrogen (Catalog no. 12634-028) containing 1% (v/v) fetal bovine serum (FBS) with penicillin (0.2 Units/mL), streptomycin (0.2 µg/mL), and 2.0 mM L-glutamine. Following incubation at 37° C. and 5% carbon dioxide for 3 days, the media is replaced with the same medium containing no serum and infection is continued for 7 more days.

Cell lysates are harvested and clarified by centrifugation (300 g for 20 minutes) and subsequently concentrated by ultrafiltration (EMD Millipore Corporation, Catalog no. UFC710008). Final concentration is obtained by ultracentrifugation for 4 hours at 112,000 g using an SW28 rotor in a Beckman Centrifuge. Virus pellets are resuspended in TNE buffer (10 mM Tris, 100 mM NaCl, 1 mM EDTA at pH 7.5) before a final polishing step using flow through cation exchange chromatography. Purified virus is stored in buffer at −80° C. for use in spiking studies.

Example 2. Determination of Minute Virus of Mice Concentrations

This example describes the process to determine the amount of minute virus of mice (MVM) in a solution. This process can be used to determine how much MVM spiked into solutions of MAB remains after treatment by activated carbon.

MVM titers are determined using a tissue culture infectious dose 50% (TCID50) assay as described in Bolton et al., Biotechnol. Appl. Biochem. Vol. 42, 2005, 133-142. Test samples are diluted to mitigate cytotoxicity and viral interference followed by 10-fold serial dilutions prepared with cell culture medium and 100 µl aliquots of each dilution are added to each of 16 wells of a 96-well microtiter plate containing sub-confluent 324K. PT cells (obtained from Professor P. Tattersall, Department of Laboratory Medicine and Genetics, Yale University School of Medicine. New Haven, Conn., USA). Following incubation at 37° C. in 5% $CO_2$ for 10-12 days, infected wells are visually assessed for cytopathic effect (CPE) and titers are determined using Spearman-Kärber methods (Spearman, C., British Journal of Psychology, Vol 2, 1908, 227-242; Kärber, G., Arch. Exp. Pathol. Pharmak. Vol 162, 1931, 480-483). Where low counts are expected (filtrate samples), large volume plating techniques are also used. Depending on the frequency of observed CPE, titer of these samples is estimated using one of several different accepted statistical methods. Log reduction values (LRVs) are calculated by determining the log 10 of the viral load upstream and subtracting the log 10 of the total virus in the filtrate.

Example 3. The Production of Xenotropic Murine Leukemia Virus

This example describes the process to prepare xenotropic murine leukemia virus (XMuLV), which represents retrovirus or retrovirus-like particles. The XMuLV is subsequently spiked into solutions of MAB and its selective removal by activated carbon is examined.

Highly purified XMuLV is produced by infecting a single flask of MV1Lu cells (Mink lung cells ATCC CCL-64) in the presence of DMEM supplemented with 10% (v/v) fetal bovine serum (FBS) with penicillin (0.2 Units/mL), streptomycin (0.2 µg/mL), and 2 mM L-glutamine. This infected flask of cells undergoes repeated passaging and expansion in DMEM supplemented with 2.5% (v/v) fetal bovine serum (FBS) with penicillin (0.2 Units/mL), streptomycin (0.2 µg/mL), and 2 mM L-glutamine. The cell culture fluid of infected monolayers is harvested and the flasks are fed with Advanced/F12 Dulbecco's Modified Eagle's Medium (Adv DMEM) Invitrogen (Catalog no. 12634-028) containing penicillin (0.2 Units/mL), streptomycin (0.2 µg/mL), and 2 mM L-glutamine. Following incubation at 37° C. 5% $CO_2$ for 2 days, the cell culture fluid of infected monolayers is harvested and the monolayers are fed again with Adv DMEM with penicillin (0.2 Units/mL), streptomycin (0.2 µg/mL), and 2 mM L-glutamine.

Following incubation at 37° C. and 5% carbon dioxide for 2 days, the cell culture fluid is harvested. All cell culture fluids are clarified by low speed centrifugation (300 g for 20 minutes), filtered through 0.45 µm Durapore filter and purified by centrifugation at 9500×g for 2 hours using GSA rotor in Sorvall centrifuge. Pelleted virus is resuspended in protein-free storage buffer and stored at −80° C. until ready for use in spiking studies.

Example 4. Determination of Xenotropic Murine Leukemia Virus Concentrations

This example describes the process to determine the amount of xenotropic murine leukemia virus (XMuLV) in a solution. This process is used to determine how much XMuLV spiked into solutions of MAB remains after treatment with activated carbon.

XMuLV titers are determined using a tissue culture infectious dose 50% (TCID50) assay as described in Bolton et al., Biotechnol. Appl. Biochem. Vol. 42, 2005, 133-142. Test samples are diluted to mitigate cytotoxicity and viral interference followed by preparation of 10-fold serial dilutions with cell culture medium, and 100 μl aliquots of each dilution are added to each of 16 wells of a 96-well microtiter plate containing sub-confluent PG4 cells (ATCC CRL-2032). The plates are then spinoculated in centrifuge (1800 rpm for 60 mins). Following incubation at 37° C. in 5% $CO_2$ for 7 days, infected wells are visually assessed for cytopathic effect (CPE) and titers are determined using the Spearman-Kärber methods (Spearman, C., British Journal of Psychology, Vol 2, 1908, 227-242; Kärber, G., Arch. Exp. Pathol. Pharmak. Vol 162, 1931, 480-483). Where low counts are expected (filtrate samples), large volume plating techniques are also used. Depending on the frequency of observed CPE, titer of these samples is estimated using one of several different accepted statistical methods. Log reduction values (LRV) is calculated by determining the log 10 of the viral load upstream and subtracting the log 10 of the total virus in the filtrate.

Example 5. Method to Determine Whether Activated Carbon can be Used to Selectively Remove a Parvovirus from a MABI Monoclonal Antibody Solution This is a representative example that demonstrates a method to determine if a parvovirus, represented by minute virus of mice (MVM), is removed from a solution containing a monoclonal antibody (i.e., MABI) by flowing through a column of activated carbon. The results indicate that activated carbon can be used to selectively remove a parvovirus from a MABI monoclonal antibody solution.

A solution of MABI is spiked with MVM and then flowed through an activated carbon column, as described below.

MABI produced from CHO cell is clarified and subsequently subjected to Protein A affinity chromatography (eluted with 25 mM acetic acid, 25 mM glycine HCl). The pH of the Protein A eluate is adjusted to pH 7.0 with 1 M Tris base and the eluate is filtered through a Stericup-GP 0.22 μm Millipore Express PLUS membrane (1 L, catalogue number: SCGPU02RE, EMD Millipore Corporation, Billerica, Mass., 01821, USA). MABI feed at pH 7.0 is spiked with Ultrapure grade of MVM that is produced according to the procedure described in Example 1 to a target amount of 2.0 E+06 $TCID_{50}$/mL. The spiked feed is filtered through a 0.22 μm GP express filter before contact with activated carbon.

A glass chromatography column (Omnifit Benchmark Column 10 mm/10) mm, 10 mm diameter, 100 mm length. SKU: 006BCC-10-10-AF, Diba Industries, Danbury, Conn. 06810, US) is loaded with 200 mg of Nuchar HD activated carbon (MeadWestVaco Corporation, Richmond, Va., USA) slurried in water. The column is packed by flowing water through it, which results in a packed column volume of 0.8 mL.

The activated carbon column is pre-equilibrated with about 10 CV of 25 mM Tris at pH 7.0. Virus spiked MAB feed is pumped through the activated carbon column at 1 mL/min (0.8 CV/min) with Watson Marlow cassette pumps. 2 ml fractions are collected from the effluent at column loads of 1.0 kg/L and 2.0 kg/L. The samples are titrated by virus infectivity assay, as described in Example 2. As summarized in Table I and FIG. 1, this experiment demonstrates that greater than 5.0 LRV of a parvovirus, represented by MVM, are removed from a solution of MABI by flowing the solution though a column of activated carbon at column loads of 1.0 kg/L and 2.0 kg/L. Accordingly, activated carbon can be used to selectively remove a parvovirus from a solution containing MABI.

TABLE I

LRV of MVM removed from MABI containing solution, measured in fractions collected at various column loads of MABI on the activated carbon column. The experiment is run in duplicate and the value listed is an average of those two values. Note that the concentration of MVM in the fractions is below the levels of detection.

| Column load of MABI on activated carbon (kg/L) | LRV of MVM from MABI |
|---|---|
| 1.0 | ≥5.03 |
| 2.0 | ≥5.13 |

Example 6. Method to Determine Whether Activated Carbon can be Used to Selectively Remove a Parvovirus from a MABII Monoclonal Antibody Solution This is a second representative example along with Example 5 that demonstrates a method to determine if a parvovirus, represented by minute virus of mice (MVM), is removed from a solution containing monoclonal antibody (i.e., MABII) by flowing through a column of activated carbon. The results indicate that activated carbon cannot be used for selectively removing a parvovirus from a MABII monoclonal antibody solution.

A solution of MABII is spiked with MVM and subsequently flowed through an activated carbon column, as described below.

MABII produced from CHO cells is clarified and then subjected to Protein A column chromatography (eluted with 25 mM acetic acid, 25 mM glycine HCl). The pH of the Protein A eluate is adjusted to pH 7.0 with 1 M Tris base and filtered through a Stericup-GP 0.22 μm Millipore Express PLUS membrane (1 L, catalogue number: SCGPU02RE, EMD Millipore Corporation. Billerica, Mass., 01821, USA). The feed is dialyzed into 25 mM Tris pH 7.0 twice with dialysis tubing (Standard RC Dialysis Trial Kits, Spectra/Por 1-3, 3.5K MWCO, 54 mm FLAT WIDTH, serial number: 132725, Spectrum Laboratories, Inc. Rancho Dominguez, Calif., 90220 USA). The solution is then filtered through a Stericup-GP 0.22 μm Millipore Express PLUS membrane (1 L, catalogue number: SCGPU02RE, EMD Millipore Corporation, Billerica, Mass., 01821, USA). The dialyzed MABII feed at pH 7.0 is spiked with Ultrapure grade of MVM that is produced according to the procedure described in Example 1 to a target amount of 2.0 E+06 $TCID_{50}$/mL. The spiked feed is then filtered through a 0.22 μm GP express filter before contacting with activated carbon.

A glass chromatography column (Omnifit Benchmark Column 10 mm/100 mm, 10 mm diameter, 100 mm length, SKU: 006BCC-10-10-AF, Diba Industries. Danbury, Conn. 06810, US) is loaded with 200 mg of Nuchar HD activated carbon (MeadWestVaco Corporation, Richmond, Va., USA) slurried in water. The column is packed by flowing water through it, which results in a packed column volume of 0.8 mL.

The activated carbon column is pre-equilibrated with about 10 CV of 25 mM Tris at pH 7.0. Virus spiked mAb feed is pumped through the activated carbon column at 1 mL/min (0.8 CV/min) with Watson Marlow cassette pumps.

2 ml fractions are collected from the effluent at column loads of 0.5 kg/L, 1.0 kg/L, and 2.0 kg/L. The samples are titrated using a virus infectivity assay, as described in Example 2.

Figure 1:
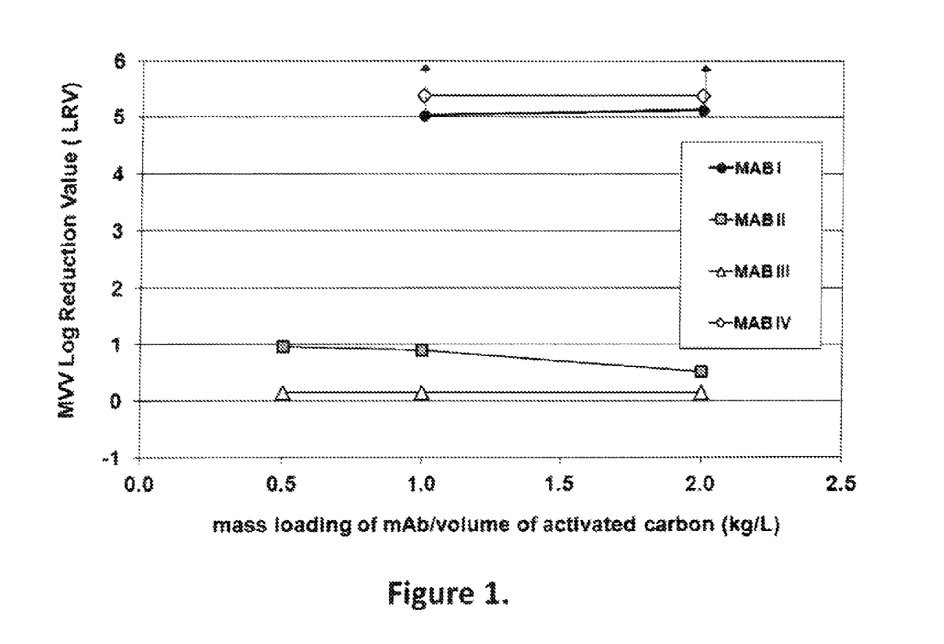
FIG. 1 is a graph depicting the results of experiments to determine if a parvovirus, represented by minute virus of mice (MVM), can be removed from a solution of monoclonal antibody by flowing the solution though a column of activated carbon, as observed for four different types of monoclonal antibody samples. MVM is removed in an amount greater than 5.0 LRV for two separate monoclonal antibody solutions, MABI and MABIV, at column loads of 1.0 kg/L and 2.0 kg/L. However, MVM is not removed in an amount above 1.0 LRV for two other monoclonal antibody solutions. MABII and MABIII, at column loads of 0.5 kg/L, 1.0 kg/L, and 2.0 kg/L. The X-axis depicts the amount (in kgs) of the monoclonal antibody that is loaded onto the column per liter (L) of activated carbon at the point a fraction is taken and the Y-axis depicts the log reduction value of the MVM virus in the fraction. The upward pointing arrows indicate that the concentration of virus in the sample is below the limits of detection for the fraction.

As summarized in Table II and FIG. 1, this experiment demonstrates that less than 1.0 LRV of parvovirus-like particles, represented by Minute Virus of Mice (MVM), are removed from a solution of MABII by flowing the solution though a column of activated carbon at column loads of 0.5 kg/L, 1.0 kg/L and 2.0 kg/L. The results indicate that activated carbon cannot be used to selectively remove a parvovirus from a MABII monoclonal antibody solution.

TABLE II

LRV of MVM removed from MABII in fractions collected at various column loads of MABII on the activated carbon column.

| Column load of MABII on activated carbon (kg/L) | LRV of MVM from MABII |
| --- | --- |
| 0.5 | 0.96 |
| 1.0 | 0.90 |
| 2.0 | 0.52 |

Example 7. Method to Determine Whether Activated Carbon can be Used to Selectively Remove a Parvovirus from a MABIII Monoclonal Antibody Solution This is a third representative example along with Example 5 and Example 6 that demonstrates a method to determine if a parvovirus, represented by MVM, is removed from a solution containing a monoclonal antibody (i.e., MABIII) by flowing through a column of activated carbon. The results indicate that activated carbon cannot be used to selectively remove a parvovirus from a MABIII monoclonal antibody solution.

A solution of MABIII is spiked with MVM and then flowed through a column of activated carbon, as described below.

MABIII is provided as a clarified cell culture by Merck Serono. MABIII is captured with Protein A chromatography (eluting with 20 mM glycine-hydrochloride buffer at pH 2.6). The pH of the MABIII eluate is adjusted to pH 7.0 with 1 M Tris base and the solution is then filtered through a Stericup-GP 0.22 μm Millipore Express PLUS membrane (1 L, catalogue number: SCGPU02RE, EMD Millipore Corporation. Billerica, Mass., 01821, USA). The feed is dialyzed into 25 mM Tris pH 7.0 twice with dialysis tubing (Standard RC Dialysis Trial Kits. Spectra/Por 1-3, 3.5K MWCO, 54 mm FLAT WIDTH, serial number: 132725, Spectrum Laboratories, Inc. Rancho Dominguez. Calif. 90220 USA). The solution is subsequently filtered through a Stericup-GP 0.22 μm Millipore Express PLUS membrane (1 L, catalogue number: SCGPU02RE, EMD Millipore Corporation, Billerica, Mass., 01821, USA).

MABIII feed at pH 7.0 is spiked with Ultrapure grade of MVM that is produced according to the procedure described in Example 1, to a target spike of 2.0E+06 $TCID_{50}$/mL. The spiked feed is then filtered through a 0.22 μm GP express filter before contacting with activated carbon.

A glass chromatography column (Omnifit Benchmark Column 10 mm/100 mm, 10 mm diameter, 100 mm length, SKU: 006BCC-10-10-AF, Diba Industries, Danbury, Conn. 06810, US) is loaded with 200 mg of Nuchar HD activated carbon (MeadWestVaco Corporation, Richmond. Va., USA) slurried in water. The column is packed by flowing water through it, which resulted in a packed column volume of 0.8 mL.

The activated carbon column is pre-equilibrated with about 10 CV of 25 mM Tris at pH7.0. Virus spiked MAB feed is pumped through the activated carbon column at 1 mL/min (0.8 CV/min) with Watson Marlow cassette pumps. 2 ml fractions are collected from the effluent at column loads of 0.5 kg/L, 1.0 kg/L, and 2.0 kg/L. The samples are titrated using a virus infectivity assay, as described in Example 2.

As summarized in Table III and FIG. 1, this experiment demonstrates that less than 1.0 LRV of parvovirus-like particles, represented by Minute Virus of Mice (MVM), are removed from a solution of MABIII by flowing the solution though a column of activated carbon at column loads of 0.5 kg/L, 1.0 kg/L and 2.0 kg/L. The results of this method indicate that activated carbon cannot be used to selectively remove parvovirus-like particles from a MABIII monoclonal antibody solution.

TABLE III

LRV of MVM removed from MABIII in fractions collected at various column loads of MABIII on an activated carbon column.

| Column load of MABIII on activated carbon (kg/L) | LRV of MVM from MABIII |
| --- | --- |
| 0.5 | 0.15 |
| 1.0 | 0.15 |
| 2.0 | 0.15 |

Example 8. Method to Determine Whether Activated Carbon can be Used to Selectively Remove a Parvovirus from a MABIV Monoclonal Antibody Solution This is a forth representative example along with Example 5, Example 6, and Example 7 that demonstrates a method to determine if a parvovirus, represented by MVM, is removed from a solution containing a monoclonal antibody (i.e., MABIV) by flowing through a column of activated carbon. The results indicate that activated carbon can be used to selectively remove a parvovirus from a MABIV monoclonal antibody solution.

A solution of MABIV is spiked with MVM and then flowed through a column of activated carbon, as described below.

MABIV monoclonal antibody is obtained from Merck Serono Biodevelopment as a 10 g/L aqueous solution containing 10 mM citric acid, 100 mM glycine, 100 mM sodium chloride, and 0.01% Tween. The feed is dialyzed into 25 mM Tris pH 7.0 twice with dialysis tubing (Standard RC Dialysis Trial Kits, Spectra/Por 1-3, 3.5K MWCO, 54 mm FLAT WIDTH, serial number: 132725, Spectrum Laboratories Inc., Rancho Dominguez, Calif., 90220 USA). The solution is filtered through a Stericup-GP 0.22 μm Millipore Express PLUS membrane (1 L, catalogue number: SCGPU02RE, EMD Millipore Corporation, Billerica, Mass., 01821. USA). MABIV feed at pH 7.0 is spiked with Ultrapure grade of MVM that is produced according to the procedure described in Example 1 to a target spike of 2.0 E+06 $TCID_{50}$/mL. The spiked feed is then filtered through a 0.22 μm GP express filter before contacting with activated carbon.

A glass chromatography column (Omnifit Benchmark Column 10 mm/100 mm, 10 mm diameter, 100 mm length, SKU: 006BCC-10-10-AF, Diba Industries, Danbury, Conn. 06810, US) is loaded with 200 mg of Nuchar HD activated carbon (MeadWestVaco Corporation, Richmond, Va., USA) slurried in water. The column is packed by flowing water through it, which results in a packed column volume of 0.8 mL.

The activated carbon column is then pre-equilibrated with about 10 CV of 25 mM Tris at pH 7.0. Virus spiked MAB feed is pumped through the activated carbon column at 1 mL/min (0.8 CV/min) with Watson Marlow cassette pumps. 2 ml fractions are collected from the effluent at column loads of 1.0 kg/L and 2.0 kg/L. The samples are titrated using a virus infectivity assay, as described in Example 2.

As summarized in Table IV and FIG. 1, this experiment demonstrates that greater than 5.0 LRV of a parvovirus, represented by MVM, is removed from a solution of MABIV by flowing the solution though a column of activated carbon at column loads of 1.0 kg/L and 2.0 kg/L. The results indicate that activated carbon can be used to selectively remove a parvovirus from a MABIV monoclonal antibody solution.

TABLE IV

LRV of MVM removed from MABIV in fractions collected at various column loads of MABIV on the activated carbon column. The experiment was run in duplicate and the value listed is an average of those two values. Note that the concentration of MVM in the fractions is below the levels of detection.

| Column load of MABIV on activated carbon (kg/L) | LRV of MVM from MABIV |
|---|---|
| 1.0 | ≥5.38 |
| 2.0 | ≥5.38 |

Example 9. Method to Determine Whether Activated Carbon can be Used to Selectively Remove Retroviruses and/or Retrovirus-Like Particles from a MABI Monoclonal Antibody Solution This is a representative example that demonstrates a method to determine if retroviruses and/or retrovirus-like particles, represented by xenotropic murine leukemia virus (XMuLV), are removed from a solution containing monoclonal antibody (i.e., MABI) by flowing through a column of activated carbon. The results indicate that activated carbon can be used to selectively remove retroviruses and retrovirus-like particles from a MABI monoclonal antibody solution.

A solution of MAB I is spiked with XMuLV and flowed through a column of activated carbon, as described below.

MAB produced in CHO cells is clarified and then isolated using Protein A column chromatography (eluted with 25 mM acetic acid, 25 mM glycine HCl). The pH of the Protein A elutate is adjusted to pH 7.0 with 1 M iris base and the solution is filtered through a Stericup-GP 0.22 µm Millipore Express PLUS membrane (1 L, catalogue number: SCGPU02RE, EMD Millipore Corporation, Billerica, Mass., 01821. USA). MABI feed at pH 7.0 is spiked with TFF purified XMuLV that is produced according to the procedure described in Example 3 to a target spike of 1.0E+05 $TCID_{50}$/mL. The spiked feed is filtered through a 0.45 µm Durapore filter before contacting with activated carbon.

A glass chromatography column (Omnifit Benchmark Column 10 mm/100 mm, 10 mm diameter, 100 mm length, SKU: 006BCC-10-10-AF, Diba Industries, Danbury, Conn. 06810, US) is loaded with 200 mg of Nuchar HD activated carbon (MeadWestVaco Corporation, Richmond, Va., USA) slurried in water. The column is packed by flowing water through it, which results in a packed column volume of 0.8 mL.

The activated carbon column was is pre-equilibrated with about 10 CV of 25 mM Tris at pH 7.0. Virus spiked MAB feed is pumped through the activated carbon column at 1 mL/min (0.8 CV/min) with Watson Marlow cassette pumps. 2 ml fractions are collected from the effluent at column loads of 0.5 kg/L, 1.0 kg/L, and 1.5 kg/L. The samples are titrated using a virus infectivity assay, as described in Example 4.

Figure 2:
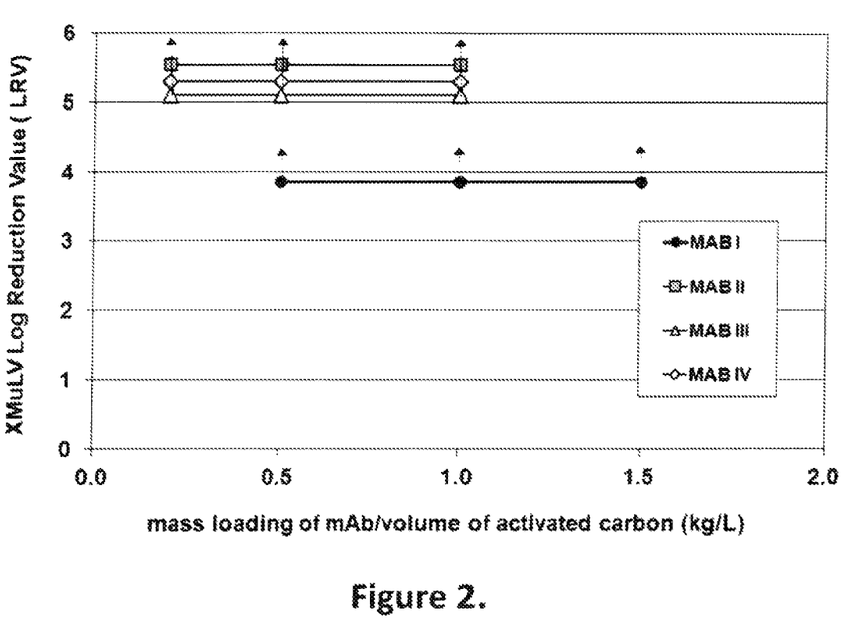
FIG. 2 is a graph depicting the results of experiments to determine if a retrovirus or retrovirus-like particle, represented by xenotropic murine leukemia virus (XMuLV), can be removed from a solution of a monoclonal antibody by flowing though a column of activated carbon, as observed for four different types of monoclonal antibody samples. XMuLV is removed in an amount greater than 3.0 LRV for MABI antibody solution at column loads of 0.5 kg/L, 1.0 kg/L, and 1.5 kg/L. XMuLV is removed in an amount greater than 5.0 LRV at column loads of 0.2 kg/L, 0.5 kg/L, and 1.0 kg/L, in case of antibody solutions, MABII, MABIII and MABIV. The X-axis depicts the amount (in kgs) of the monoclonal antibody that is loaded onto the column per liter (L) of activated carbon at the point a fraction is taken and the Y-axis depicts the log reduction value of the XMuLV virus in the fraction. The upward pointing arrows indicate that the concentration of virus in the sample is below the limits of detection for the fraction.

As summarized in Table V and FIG. 2, this experiment demonstrates that greater than 3.0 LRV of retroviruses and retrovirus-like particles, represented by XMuLV, are removed from a solution of MABI by flowing the solution though a column of activated carbon at column loads of 0.5 kg/L, 1.0 kg/L, and 1.5 kg/L. The results indicate that activated carbon can be used to selectively remove retrovirus-like particles from a MABI monoclonal antibody solution.

TABLE V

LRV of XMuLV removed from MABI in fractions collected at various column loads of MABI on an activated carbon column. The experiment was run in duplicate and the value listed is an average of those two values. Note that the concentration of XMuLV in the fractions is below the levels of detection.

| Column load of MABI on activated carbon (kg/L) | LRV of XMuLV from MABI |
|---|---|
| 0.5 | ≥3.85 |
| 1.0 | ≥3.85 |
| 1.5 | ≥3.85 |

Example 10. Method to Determine Whether Activated Carbon can be Used to Selectively Remove Retroviruses and/or Retrovirus-Like Particles from a MABII Monoclonal Antibody Solution This is a second representative example along with Example 9 that demonstrates a method to determine if retroviruses and retrovirus-like particles, represented by XMuLV, are removed from a solution containing monoclonal antibody (i.e., MABII) by flowing through a column of activated carbon. The results indicate that activated carbon can be used to selectively remove retroviruses and retrovirus-like particles from a MABII monoclonal antibody solution.

A solution of MABII is spiked with XMuLV and flowed through a column of activated carbon, as described below.

MABII produced in CHO cell is clarified and then isolated using Protein A column chromatography (eluted with 25 mM acetic acid, 25 mM glycine HCl). The pH of the Protein A eluate is adjusted to pH 7.0 with 1 M Tris base and then the solution is filtered through a Stericup-GP 0.22 µm Millipore Express PLUS membrane (1 L, catalogue number: SCGPU02RE, EMD Millipore Corporation, Billerica, Mass., 01821, USA). The feed is subsequently dialyzed into 25 mM Tris pH 7.0 twice with dialysis tubing (Standard RC Dialysis Trial Kits, Spectra/Por 1-3, 3.5K MWCO, 54 mm FLAT WIDTH, serial number: 132725. Spectrum Laboratories Inc., Rancho Dominguez, Calif., 90220 USA). The solution is filtered through a Stericup-GP 0.22 µm Millipore Express PLUS membrane (1 L, catalogue number: SCGPU02RE, EMD Millipore Corporation, Billerica. Mass. 01821, USA).

MABII feed at pH 7.0 is spiked with Ultrapure grade of XMuLV that is produced according to the procedure described in Example 3 to a target spike of 1.0E+06 TCID$_{50}$/mL. The spiked feed is filtered through a 0.45 µm Durapore filter before contacting with activated carbon.

A glass chromatography column (Omnifit Benchmark Column 10 mm/100 mm, 10 mm diameter, 100 mm length, SKU: 006BCC-10-10-AF. Diba Industries, Danbury, Conn. 06810, US) is loaded with 200 mg of Nuchar HD activated carbon (MeadWestVaco Corporation, Richmond, Va., USA) slurried in water. The column is packed by flowing water through it, which results in a packed column volume of 0.8 mL.

The activated carbon column is pre-quilibrated with about 10 CV of 25 mM Tris at pH 7.0. Virus spiked MAB feed is pumped through the activated carbon column at 1 mL/min (0.8 CV/min) with Watson Marlow cassette pumps. 2 ml fractions are collected from the effluent at column loads of 0.2 kg/L, 0.5 kg/L, and 1.0 kg/L. The samples are titrated using a virus infectivity assay, as described in Example 4.

As summarized in Table VI and FIG. 2, this experiment demonstrates that greater than 5.0 LRV of retroviruses and retrovirus-like particles, represented by XMuLV, are removed from a solution of MABII by flowing the solution though a column of activated carbon at column loads of 0.2 kg/L, 0.5 kg/L, and 1.0 kg/L. The results indicate that activated carbon can be used to selectively remove retroviruses and retrovirus-like particles from a MABII monoclonal antibody solution.

TABLE VI

LRV of XMuLV removed from MABII in fractions collected at various column loads of MABII on the activated carbon column. Note that the concentration of XMuLV in the fractions is below the levels of detection.

| Column load of MABII on activated carbon (kg/L) | LRV of XMuLV from MABII |
|---|---|
| 0.2 | ≥5.54 |
| 0.5 | ≥5.54 |
| 1.0 | ≥5.54 |

Example 11. Method to Determine Whether Activated Carbon can be Used to Selectively Remove Retroviruses and/or Retrovirus-Like Particles from a MABIII Monoclonal Antibody Solution This is a third representative example along with Example 9 and Example 10 demonstrates a method to determine if retroviruses and retrovirus-like particles, represented by XMuLV, are removed from a solution containing a monoclonal antibody (i.e., MABIII) by flowing through a column of activated carbon. The results indicate that activated carbon can be used to selectively remove retroviruses and retrovirus-like particles from a MABIII monoclonal antibody solution.

A solution of MABIII is spiked with XMuLV and flowed through a column of activated carbon, as described below.

MABIII is provided by Merck Serono as a clarified cell culture. It is captured using Protein A chromatography (eluting with 20 mM glycine-hydrochloride buffer at pH 2.6). The eluate has high levels of HCP and is therefore purified a second time using Protein A column chromatography. Before loading the chromatography column, the sodium chloride concentration of the MABIII solution is increased to 0.5 M. The MABIII antibody is then eluted with 25 mM acetic acid, 25 mM glycine HCl. The pH of the MABIII eluate is adjusted to pH 7.0 with 1 M Tris base and the solution is filtered through a Stericup-GP 0.22 µm Millipore Express PLUS membrane (1 L, catalogue number: SCGPU02RE, EMD Millipore Corporation. Billerica, Mass., 01821. USA). The feed is dialyzed into 25 mM Tris pH 7.0 twice with dialysis tubing (Standard RC Dialysis Trial Kits, Spectra/Por 1-3, 3.5K MWCO, 54 mm FLAT WIDTH, serial number: 132725, Spectrum Laboratories, Inc. Rancho Dominguez, Calif., 90220 USA). The solution is filtered through a Stericup-GP 0.22 µm Millipore Express PLUS membrane (1 L, catalogue number: SCGPU02RE, EMD Millipore Corporation, Billerica, Mass., 01821, USA).

MAB III feed at pH 7.0 is spiked with Ultrapure grade of XMuLV that is produced according to the procedure described in Example 3 to a target spike of 1.0E+06 TCID$_{50}$/mL. The spiked feed is filtered through a 0.45 µm Durapore filter before contacting with activated carbon.

A glass chromatography column (Omnifit Benchmark Column 10 mm/100 mm, 10 mm diameter, 100 mm length, SKU: 006BCC-10-10-AF, Diba Industries, Danbury, Conn. 06810, US) is loaded with 200 mg of Nuchar HD activated carbon (MeadWestVaco Corporation, Richmond, Va., USA) slurried in water. The column is packed by flowing water through it, which results in a packed column volume of 0.8 mL.

The activated carbon column is pre-equilibrated with about 10 CV of 25 mM Tris at pH 7.0. Virus spiked MAB feed is pumped through the activated carbon column at 1 mL/min (0.8 CV/min) with Watson Marlow cassette pumps. 2 ml fractions are collected from the effluent at column loads of 0.2 kg/L, 0.5 kg/L, and 1.0 kg/L. The samples are titrated using a virus infectivity assay, as described in Example 4.

As summarized in Table VII and FIG. 2, this experiment demonstrates that greater than 5.0 LRV of retroviruses and retrovirus-like particles, represented by XMuLV, are removed from a solution of MABIII by flowing the solution though a column of activated carbon at column loads of 0.2 kg/L, 0.5 kg/L, and 1.0 kg/L. The results indicate that activated carbon can be used to selectively remove retroviruses and retrovirus-like particles from a MABIII monoclobal antibody solution.

TABLE VII

LRV of XMuLV removed from MABIII in fractions collected at various column loads of MABIII on an activated carbon column. Note that the concentration of XMuLV in the fractions is below the levels of detection.

| Column load of MABIII on activated carbon (kg/L) | LRV of XMuLV from MABIII |
|---|---|
| 0.2 | ≥5.10 |
| 0.5 | ≥5.10 |
| 1.0 | ≥5.10 |

Example 12. Method to Determine Whether Activated Carbon can be Used to Selectively Remove Retroviruses and/or Retrovirus-Like Particles from a MABIV Monoclonal Antibody Solution This is a forth representative example along with Example 9, Example 10, and Example 11 that demonstrates a method to determine if retroviruses and retrovirus-like particles, represented by XMuLV, are removed from a solution containing a monoclonal antibody (i.e., MABIV) by flowing through a column of activated carbon. The results indicate that activated carbon can be used to selectively remove retroviruses and retrovirus-like particles from a MABIV monoclonal antibody solution.

A solution of MABIV is spiked with XMuLV and flowed through a column of activated carbon, as described below.

MABIV monoclonal antibody is obtained from Merck Serono Biodevelopment as a 10 g/L aqueous solution containing 10 mM citric acid, 100 mM glycine, 100 mM sodium chloride, and 0.01% of Tween. The feed is then dialyzed into 25 mM Tris pH 7.0 twice with dialysis tubing (Standard RC Dialysis Trial Kits, Spectra/Por 1-3, 3.5K MWCO, 54 mm FLAT WIDTH, serial number: 132725, Spectrum Laboratories Inc., Rancho Dominguez, Calif., 90220 USA). The solution is filtered through a Stericup-GP 0.22 µm Millipore Express PLUS membrane (1 L, catalogue number: SCGPU02RE, EMD Millipore Corporation, Billerica, Mass., 01821, USA). MABIV feed at pH 7.0 is spiked with Ultrapure grade of XMuLV that is produced according to the procedure described in Example 3 to a target spike of 1.0E+06 $TCID_{50}$/mL. The spiked feed is filtered through a 0.45 µm Durapore filter before contacting with activated carbon.

A glass chromatography column (Omnifit Benchmark Column 10 mm/100 mm, 10 mm diameter, 100 mm length, SKU: 006BCC-10-10-AF, Diba Industries, Danbury, Conn. 06810, US) is loaded with 200 mg of Nuchar HD activated carbon (MeadWestVaco Corporation, Richmond, Va., USA) slurried in water. The column is packed by flowing water through it, which results in a packed column volume of 0.8 mL.

The activated carbon column is pre-equilibrated with about 10 CV of 25 mM Tris at pH 7.0. Virus spiked MAB feed is pumped through the activated carbon column at 1 mL/min (0.8 CV/min) with Watson Marlow cassette pumps. 2 ml fractions are collected from the effluent at column loads of 0.2 kg/L, 0.5 kg/L, and 1.0 kg/L. The samples are titrated using a virus infectivity assay, as described in Example 4.

As summarized in Table VIII and FIG. 2, this experiment demonstrates that greater than 5.0 LRV of retroviruses and retrovirus-like particles, represented by (XMuLV, are removed from a solution of MABIV by flowing the solution though a column of activated carbon using at column loads of 0.2 kg/L, 0.5 kg/L, and 1.0 kg/L. The results indicate that activated carbon can be used to selectively remove retroviruses and retrovirus-like particles from a MABIV monoclonal antibody solution.

TABLE VIII

LRV of XMuLV removed from MABIV in fractions collected at various column loads of MABIV on a activated carbon column. The experiment was run in duplicate and the value listed is an average of those two values. Note that the concentration of XMuLV in the fractions is below the levels of detection.

| Column load of MABIV on activated carbon (kg/L) | LRV of XMuLV from MABIV |
|---|---|
| 0.2 | ≥5.29 |
| 0.5 | ≥5.29 |
| 1.0 | ≥5.29 |

The specification is most thoroughly understood in light of the teachings of the references cited within the specification which are hereby incorporated by reference. The embodiments within the specification provide an illustration of embodiments in this invention and should not be construed to limit its scope. The skilled artisan readily recognizes that many other embodiments are encompassed by this invention. All publications and inventions are incorporated by reference in their entirety. To the extent that the material incorporated by reference contradicts or is inconsistent with the present specification, the present specification will supercede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

The invention claimed is:

1. A method for determining whether activated carbon can be used for the removal of viruses from a sample containing a target protein having a protein concentration equal to or greater than 0.2 g/L, the method comprising the steps of: (a) providing a portion of a sample comprising a target protein having a protein concentration equal to or greater than 0.2 g/L: (b) adding a virus to the portion of the sample in the amount ranging from $10^4$ to $10^9$ PFU/mL; (c) flowing the portion of the sample through a column packed with activated carbon; (d) collecting one or more flow-through fractions from the column; and (e) measuring the virus amount in the one or more flow-through fractions, wherein a reduction in the virus amount in the one or more flow-through fractions by at least 3.0 LRV is indicative that activated carbon can be used for the removal of viruses from the sample.

2. The method of claim 1, wherein the sample comprises a protein concentration equal to or greater than 0.5 g/L.

3. The method of claim 1, wherein the sample comprises a protein concentration equal to or greater than 1 g/L.

4. The method of claim 1, wherein the sample comprises a pH in the range of 3.0-10.0 and/or a salt concentration less than 0.5M.

5. The method of claim 1, wherein the virus is a parvovirus.

6. The method of claim 5, wherein the parvovirus is minute virus of mice virus.

7. The method of claim 1, wherein the sample comprises a cell culture feed.

8. The method of claim 7, wherein the cell culture feed is a CHO cell culture feed.

9. The method of claim 1, wherein the target protein is a recombinant protein.

10. The method of claim 1, wherein the target protein is a therapeutic protein.

11. The method of claim 1, wherein the target protein is an antibody.

12. The method of claim 11, wherein the antibody is a monoclonal antibody.

13. The method of claim 1, wherein the sample comprises a clarified cell culture feed.

14. The method of claim 13, wherein clarified cell culture feed is obtained using one or more methods selected from centrifugation, settling, depth filtration, screen filtration, flocculation, use of a stimulus responsive polymers and pH change.

15. The method of claim 1, wherein the sample comprises an eluate obtained from a Protein A chromatography column, wherein the eluate comprises the target protein.

16. The method of claim 1, wherein step (e) employs one or more methods selected from the group consisting of 50% tissue culture infectious dose (TCID50) assay, plaque-forming unit assay, focus-forming unit assay, lethal dose 50% assay, hemagglutination assay, fluorescent focus assay (FFA), bicinchoninic acid assay (BCA), single radial immunodiffusion assay (SRID), quantitative polymerase chain reaction (qPCR), enzyme-linked immunosorbent assay (ELISA), and transmission electron microscopy.

* * * * *